United States Patent [19]

Smith

[11] Patent Number: 5,103,827
[45] Date of Patent: Apr. 14, 1992

[54] APPARATUS FOR AND A METHOD OF DISTINGUISHING ULTRASOUND SIGNALS RETURNED FROM BUBBLES AND PARTICLES MOVING IN A FLUID FROM SIGNALS DUE TO ULTRASOUND TRANSDUCER MOTION

[75] Inventor: George H. Smith, Palo Alto, Calif.

[73] Assignee: MedaSonics, Inc., Fremont, Calif.

[21] Appl. No.: 627,237

[22] Filed: Dec. 14, 1990

[51] Int. Cl.$^5$ .............................................. A61B 8/02
[52] U.S. Cl. ...................... 128/661.08; 128/DIG. 13; 128/661.09; 73/861.25
[58] Field of Search ...................... 128/661.07, 661.08, 128/661.09, DIG. 13, 660.01; 73/861.25

[56] References Cited

U.S. PATENT DOCUMENTS

| | | | |
|---|---|---|---|
| 3,974,681 | 8/1976 | Namery | 128/DIG. 13 |
| 4,487,601 | 12/1984 | Lindemann | 128/DIG. 13 |
| 4,777,958 | 10/1988 | Ophir | 128/660.01 |
| 4,928,698 | 5/1990 | Bonnefous | 128/661.09 |
| 4,993,418 | 2/1991 | Weaver et al. | 128/661.08 |

OTHER PUBLICATIONS

Doppler Developments in the Last Quinquenium, P. T. Wells and R. Skidmore, *Ultrasound in Medicine and Biology*, 11: pp. 613-623, 1985.
Detection of Middle Cerebral Artery Emboli During Carotid Endarterectomy Using Transcranial Doppler Ultrasonography, *Stroke*, vol. 21, No. 3, Mar. 1990, pp. 415-423.
Computerised Techniques for Detecting Gaseous Microemboli in Blood Using Pulsed Doppler Ultrasound, *Perfusion*, 2:213-218, 1987.

*Primary Examiner*—Francis Jaworski
*Assistant Examiner*—George Manuel
*Attorney, Agent, or Firm*—Fliesler, Dubb, Meyer & Lovejoy

[57] ABSTRACT

A method and apparatus for distinguishing ultrasound signals returned from bubbles and particles moving in a fluid from signals due to ultrasound transducer motion monitors the receiving ultrasound signal for signals which are of much larger amplitude than the signals observed when no gas bubbles or particles are present. When a large amplitude event is detected, the maximum amplitude of the forward flow signal (that is, the positive frequency portion of the power spectrum) is compared to the maximum amplitude of the reverse flow signal (negative frequency portion of the power spectrum). If these maxima are significantly different in amplitude, the event is counted as a bubble. If the maximum amplitudes of the forward and reverse flow signals are comparable, the event is classified as a motion artifact. Displays of the spectra are marked whenever an event is counted as an air or particulate emboli so as to call attention to the event and, optionally, to generate an audible or visual alarm.

8 Claims, 3 Drawing Sheets

FIG. 5
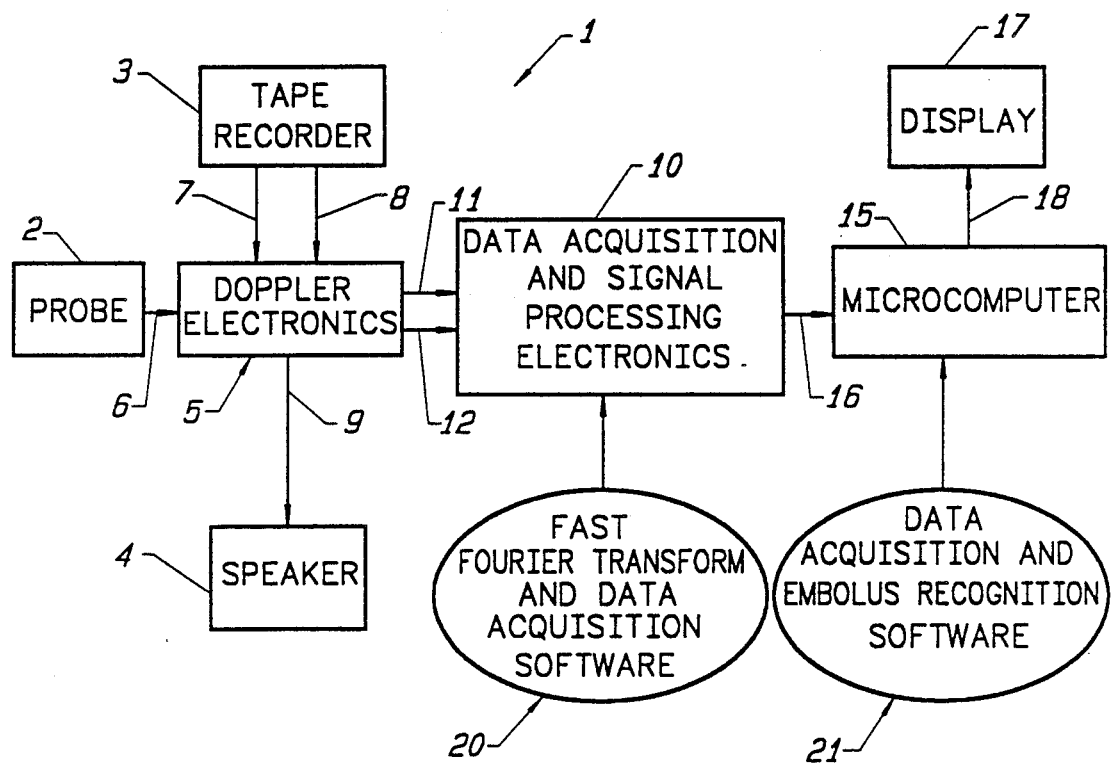
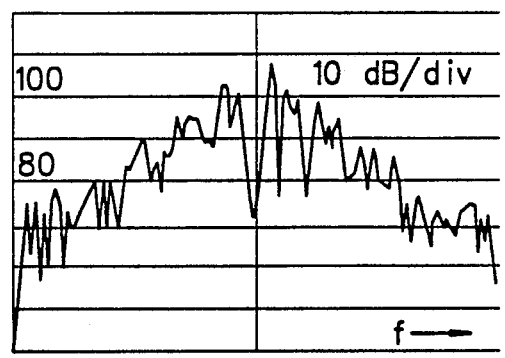
FIG. 6

5,103,827

APPARATUS FOR AND A METHOD OF DISTINGUISHING ULTRASOUND SIGNALS RETURNED FROM BUBBLES AND PARTICLES MOVING IN A FLUID FROM SIGNALS DUE TO ULTRASOUND TRANSDUCER MOTION

BACKGROUND OF THE INVENTION

1. Field of the Invention

The present invention relates to a method and an apparatus for measuring fluid flow using Doppler ultrasound techniques in general and in particular to a method and an apparatus for distinguishing ultrasound signals returned from moving gas bubbles or solid particles in a fluid from signals due to ultrasound transducer motion.

2. Description of the Prior Art

Doppler ultrasound has been used for many years to measure the flow rate of fluids that contain particles which reflect sound energy and shift the frequency of this sound in a direction and by an amount proportional to the direction and velocity of movement of the particles relative to an ultrasound transducer. See, for example, P. T. Wells and R. Skidmore, "Doppler Developments in the Last Quinquenium", *Ultrasound in Medicine and Biology*, 11:p. 613–623, 1985.

When a reflected frequency modulated ultrasound signal is received, it is typically converted to a lower frequency, e.g. d.c., to remove the carrier and provide an audio baseband signal. The baseband signal is then digitized. A Fourier transform of the digitized baseband signal is then used to produce a spectrum of the power at each frequency therein. The spectrum, which contains both positive and negative frequency components corresponding to changes in the velocity of the fluid flow in a forward and a reverse direction, is then used to distinguish flow towards the transducer from flow away from the transducer.

Referring to FIGS. 1 and 2, there is shown, respectively, a typical power spectrum output from a spectrum analyzer for cases of forward fluid flow (flow toward the transducer) and reverse fluid flow (flow away from the transducer). Forward flow corresponds to signal energy in the positive frequency portion of the power spectrum; i.e., the signal to the right of the vertical center line in FIGS. 1 and 2. Similarly, reverse flow is represented by the negative frequency portion of the power spectrum—the signal to the left of the center line in FIGS. 1 and 2. The amplitude of the power spectrum at each frequency corresponds to the percentage of the total volume of fluid flowing at a particular velocity. For example, as shown in FIG. 1, the highest percentage of the total volume of fluid is flowing toward the transducer at a velocity corresponding to frequency $f_1$ and a substantially equivalent percentage of the total volume of fluid is flowing toward the transducer at a velocity corresponding to the frequency $f_2$. In FIG. 2, the highest percentage of the total volume of fluid is flowing away from the transducer at a velocity corresponding to the frequency $f_3$. The spectrum to the left of the centerline in FIG. 1 and to the right of the centerline in FIG. 2 is mainly noise.

When a gas bubble (or solid particle) passes in front of an ultrasound beam, the discontinuity in acoustic impedance at the gas-fluid interface (or particle-fluid interface) causes a strong reflection which can be detected by the ultrasound receiver.

Referring to FIG. 3, there is shown a typical power spectrum of a Doppler signal from a gas bubble. To the right of the centerline there is a large amplitude signal showing a flow of the bubble in a forward direction. The existence of such strong reflections due to gas bubbles or particles has been noted by Spencer et al in an article entitled, "Detection of Middle Cerebral Artery Emboli During Carotid Endarterectomy Using Transcranial Doppler Ultrasonography", Stroke, Vol. 21, No. 3, March 1990, p. 415–423, where it was reported that such emboli can be recognized by the strong signal returns they generate, and by a characteristic chirping character of the received signal. The chirping described implies that the returned signal shows a continuous change in velocity of the strong reflection from the bubble.

Previously, Padayachee et al, in an article entitled, "Computerised Techniques for Detecting Gaseous Microemboli in Blood Using Pulsed Doppler Ultrasound", *Perfusion*, 2:213–218, 1987, described two methods of bubble detection: one which employed the high amplitude of the return from a bubble, and one which used the broad spectral shape of the return which is due to the overload of the Doppler electronics from the strong response.

When a medical Doppler transducer is moved on the skin, large return signals, similar to those obtained from emboli, are generated.

While Padayachee et al, supra, recognize the high amplitude returns generated from embolic events, no mention is made of any apparatus or method for distinguishing these returns from returns due to probe motion. On the other hand, Spencer et al, supra, describe an ability to audibly distinguish between emboli (bubbles) and probe motion artifacts. However, there does not appear to be any clear quantitative criteria given by which such distinctions can be made mechanically and automatically. For example, as published by Spencer et al in their article, signals in spectrograms indicative of probe motion are not readily distinguishable from signals seen in the spectrograms of returns due to emboli. Both appear to exhibit high amplitude, broad spectrum signals with concentrations of energies in the low frequency ranges toward zero. Thus, if a bubble detection apparatus is limited to simply monitoring the returned Doppler signal for large amplitude signals, the apparatus would falsely report all probe motion artifacts as bubbles or particles. These false alarms would seriously impair the use of the apparatus for monitoring applications, since the users would lose confidence in the accuracy of the apparatus.

SUMMARY OF THE INVENTION

In view of the foregoing, principal objects of the present invention are a method and an apparatus using Doppler techniques for mechanically and automatically distinguishing emboli from Doppler probe motion.

Careful analysis of range gated, pulsed Doppler ultrasound signals returned from gas bubbles flowing through the arteries of patients undergoing cardiac surgery indicates that the received signal is often not a continuous chirp as reported by Spencer et al, but instead is often comprised of distinct sections which exhibit different, but relatively constant velocities.

Referring to FIG. 4, there is shown a time domain plot of a typical return from a single bubble. Conventional spectrum analyzers typically lack the time resolution necessary to distinguish the separate sections of this signal, and smear the signal into a continuous, sloping line instead of short, horizontal lines at separate frequencies. The distinct time domain sections of the signal returned from the gas bubbles may correspond to reflection from various surfaces of the vibrating bubble. These signals are typically significantly larger than the signals returned by blood that is free from emboli, and this large amplitude is the aspect of the signal that is used in the prior known bubble detection schemes. However, if the signal is too large, the electronics of the spectrum analyzer can become saturated, causing the analyzer to indicate energy at a broad range of frequencies, giving rise to the broad spectral shape observed by Padayachee et al. This saturation must be avoided by the Doppler electronics to preserve the unidirectional Doppler response to emboli.

In accordance with the present invention, it is recognized that the large amplitude signals from probe motion artifacts are not due to reflections of the transmitted ultrasound pulses, but are independently generated sound waves caused by the probe motion. Since these waves are not synchronous with the transmitted ultrasound pulses, the motion artifacts are manifested in both forward and reverse flow sides of the spectrum. If large amplitude returns are found with flow in the forward direction at similar amplitude to flow in the reverse direction, the returns are attributed to motion artifact rather than air bubbles or particles.

Accordingly, the apparatus of the present invention monitors the received ultrasound signal for signals which are of much larger amplitude than the signals observed when no gas bubbles or particles are present. When a large amplitude event is detected, the maximum amplitude of the forward flow signal (that is, the positive frequency portion of the power spectrum) is compared to the maximum amplitude of the reverse flow signal (negative frequency portion of the power spectrum). If these maxima are significantly different in amplitude, the event is counted as a bubble; if the maximum amplitudes of forward and reverse flow are comparable, the event is classified as a motion artifact.

The method and apparatus of the present invention can fail to detect small emboli which do not reflect enough signal to classify them as large amplitude events, or if the return signal is so large that it saturates the Doppler electronics. However, by judicious choice of the signal thresholds involved using the minimum power required for an adequate signal and an electronic design with adequate dynamic range, the method and apparatus of the present invention provide a useful index of embolic events.

BRIEF DESCRIPTION OF THE DRAWINGS

The above and other objects, features and advantages of the present invention will become apparent from the following detailed description of the accompanying drawings, in which:

FIG. 5 is a block diagram of apparatus according to the present invention; and

FIG. 6 is a typical power spectrum of Doppler signals due to probe motion.

DETAILED DESCRIPTION OF A PREFERRED EMBODIMENT

Figure 1:
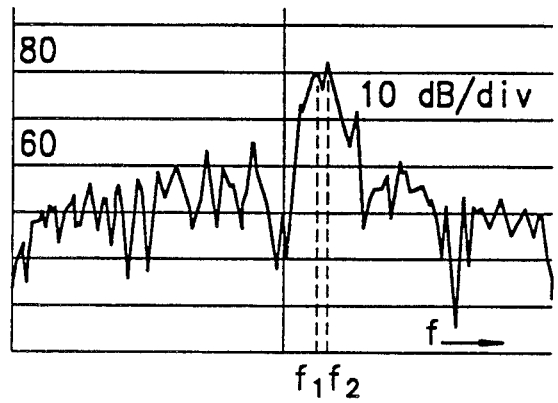
FIG. 1 is a typical power spectrum of fluid flow toward a Doppler transducer.

Referring to FIG. 5, there is provided in accordance with the present invention a block diagram of an emboli (bubble) detection apparatus designated generally as 1. In the apparatus 1 there is provided a Doppler probe 2, a tape recorder 3 and a speaker 4. The probe 2, tape recorder 3 and speaker 4 are coupled to Doppler electronics designated generally as 5 by means a plurality of signal lines 6, 7, 8 and 9. The output of Doppler electronics 5 is coupled to data acquisition and signal processing electronics designated generally as 10 by means of a pair of signal lines 11 and 12. The output of the electronics 10 is coupled to a microcomputer 15 by means of a signal line 16. A display 17 is coupled to the microcomputer 15 by means of a signal line 18. The electronics 10 are programmed by Fast Fourier Transform and data acquisition software designated generally as 20 and the microcomputer 15 is programmed with data acquisition and embolus recognition software designated generally as 21. Except as hereinafter described, the software is of a conventional nature.

The microcomputer 15 comprises, for example, a standard PC/AT style microcomputer such as a Jameco JE3010 from Jameco Electronics, Belmont, California. The Doppler electronics 5 comprises Transpect circuit cards from a standard Transpect Transcranial Doppler (TCD) unit available from Medasonics, Inc. of Fremont, California. Specifically, the circuit cards comprise a Doppler front end board Part No. 109-0184-010 and a Doppler control board Part No. 109-183-010. The data acquisition and signal processing electronics 10 comprises a data acquisition board Part No. DSP-56 from Ariel Corp., Highland Park, New Jersey.

In operation during open-heart surgery, a standard Transpect Transcranial Doppler (TCD) from Medasonics, Inc. was used to collect blood flow signals from a patient's middle cerebral artery. It is not uncommon for air bubbles to enter the arterial vessels during certain phases of such surgery. The analog forward and reverse flow signals from the TCD were then captured on the tape recorder 3. As shown in block diagram 5, the tape recorder outputs were then fed into the Doppler electronics 5 comprising the above-identified Doppler front end board and Doppler control board. The boards convert the forward and reverse flow signals into quadrature signals I and Q which are output to the data acquisition board in the data acquisition and signal processing electronics 10. The above-described software which is provided for the electronics 10 converts the analog I and Q quadrature signals into digital form at a 12.5 KHz rate, simultaneously sampling both quadrature channels. The data is then collected by the microcomputer 15 and stored on a disk. Fast Fourier Transforms of this stored data are then computed by the DSP-56 board on sequential, 128-sample blocks after applying a standard Hamming window function to each block.

Figure 2:
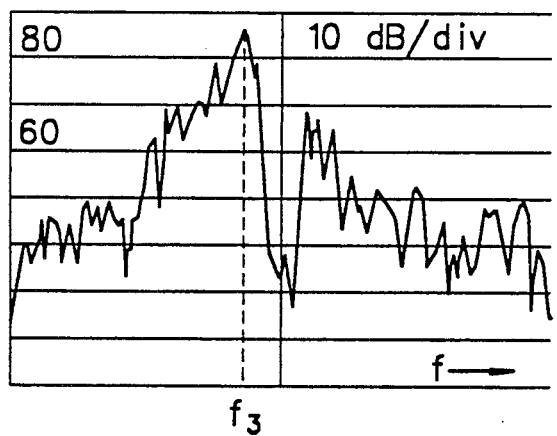
FIG. 2 is a typical power spectrum of fluid flow away from a Doppler transducer.

As discussed above, in the absence of emboli or probe motion the resulting power spectrum from the Fourier analysis appears as shown in FIG. 1 for fluid flow toward the transducer or as in FIG. 2 for fluid flow away from the transducer. When an embolus is detected, the resulting power spectrum from the Fourier analysis appears as in FIG. 3 wherein the large amplitude signal to the right of the centerline reflects the detection of an emboli moving toward the transducer.

Referring to FIG. 6, there is shown a power spectrum from a Fourier analysis due to probe motion.

Figure 3:
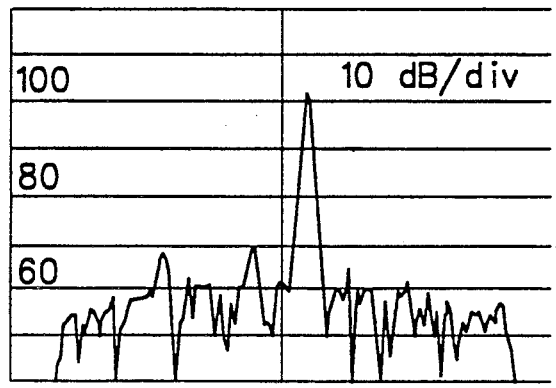
FIG. 3 is a typical power spectrum of Doppler signals from a gas bubble.
Figure 4:
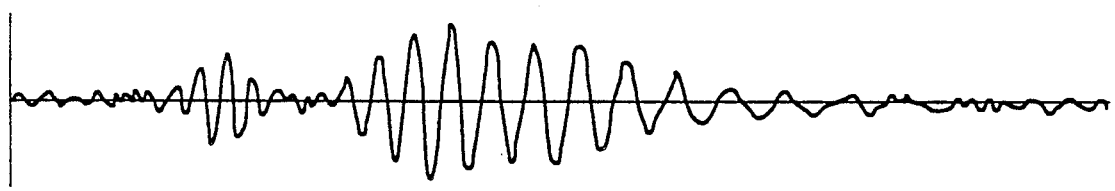
FIG. 4 is a diagram of a Doppler signal from a gas bubble in the time domain.

In practice, the apparatus of the present invention monitors the received ultrasound signals for signals which are of a much larger amplitude than the signals observed when no gas bubbles or particles are present and generates a sequence of discrete Fourier spectra of said signals. Each of the spectra comprises forward flow signals corresponding to fluid movement in a forward direction and reverse flow signals corresponding to fluid flow in a reverse direction. The apparatus then measures the peak value of each spectrum to determine an average peak or background value for the sequence. After an average peak spectral value is determined, a threshold level of at least 15 dB above the average peak spectral value is set. For example, the average peak spectral value of the spectra of FIGS. 1 and 2 is approximately 80 dB. If a threshold level of 20 dB above the average peak spectral value is set, the threshold level would be approximately 100 dB. Any peak value above threshold is then considered to be a large amplitude event. When a large amplitude event is detected, the maximum amplitude of the forward flow signal, that is, the positive frequency portion of the power spectrum, is compared to the maximum amplitude of the reverse flow signal (negative frequency portion of the power spectrum). If these maxima are significantly different in amplitude, for example, one exceeds the other by at least 10 dB, the event is counted as a bubble as shown in FIG. 3. However, if the maximum amplitudes of the forward and reverse flow are comparable, i.e. do not exceed one another by an amount within the above range, as shown in FIG. 6, the event is classified as a motion artifact.

In practice, each power spectrum is shown on the display 17 as a vertical line which changes color along a vertical frequency axis depending on the intensity of the spectrum. After applying the embolus recognition method described above, sections of the collected data which are classified as air or particulate emboli, are marked on display as by highlighting the vertical line of the spectra involved. Of course, other techniques may be employed for distinguishing between air or particulate emboli and probe motion on the display and audible alarms may also be used.

Real time monitoring of air or particulate emboli may be done with the apparatus of the present invention by avoiding the use of the tape recorder 3 and coupling the output of the probe 2 directly to the Doppler electronics 5 as shown in FIG. 5.

In still another embodiment of the present invention, the speaker 4 is coupled to the Doppler electronics 5 so as to provide a means for audibly monitoring the output signals from the probe 2 or tape recorder 3.

While preferred embodiments of the present invention are described above, it is contemplated that various modifications may be made thereto without departing from the spirit and scope of the present invention. For example, the above-described threshold level of at least 15 dB above the average peak spectral value is chosen to set a balance between the number of false alarms which occur and the number of embolic events which go undetected. This value can be changed up or down depending on the characteristics of the fluid involved. Similarly, the minimum difference between forward and reverse peaks may be changed up or down depending on the probe motion artifacts anticipated. Accordingly, it is intended that the embodiments described be considered only as an illustrative of the present invention and that the scope thereof should not be limited thereto but be determined by reference to the claims hereinafter provided and their equivalents.

What is claimed is:

1. An apparatus for distinguishing ultrasound Doppler signals returned from bubbles and particles moving in a fluid from signals due to probe motion comprising:

means for generating a sequence of discrete Fourier spectra of said signals returned from bubbles and particles moving in the fluid and said signals due to probe motion, each of said spectra comprising positive frequency components corresponding to fluid movement in a forward direction and negative frequency components corresponding to fluid movement in a reverse direction;

means for measuring the magnitude of the power in the strongest one of the positive and negative frequency components in each spectrum in said sequence;

means for determining the average value of said power;

means for setting a threshold level at a first predetermined magnitude above said average value of said power;

means for comparing the power of the strongest positive frequency component, designated the positive peak value, to the power of the strongest negative frequency component, designated the negative peak value in each spectrum, so long as either the positive peak value or the negative peak value or both in each spectrum exceeds said threshold level; and means for providing an audible or visual indication whenever the larger of said positive and negative peak values in a spectrum exceeds said first predetermined magnitude and the larger of said positive and negative peak values in the spectrum is more than a second predetermined magnitude above the other peak value, said audible or visual indication corresponding to the detection of a bubble or particle moving in said fluid as distinguished from probe motion.

2. An apparatus according to claim 1 wherein said means for generating a sequence of discrete Fourier spectra of said signals returned from bubbles and particles moving in the fluid and said signals due to probe motion comprises means for providing a predetermined number of samples of said signals returned from bubbles and particles moving in the fluid and said signals due to probe motion for each spectrum in said sequence.

3. An apparatus according to claim 2 wherein said predetermined number of samples comprises approximately 128 samples.

4. An apparatus according to claim 1 wherein said first predetermined magnitude is approximately 15 dB and said second predetermined magnitude is approximately 10 dB.

5. A method of distinguishing ultrasound Doppler signals returned from bubbles and particles moving in a fluid from signals due to probe motion comprising the steps of:

generating a sequence of discrete Fourier spectra of said signals returned from bubbles and particles moving in the fluid and said signals due to probe motion, each of said spectra comprising positive frequency components corresponding to fluid movement in a forward direction and negative frequency components corresponding to fluid movement in a reverse direction;

measuring the magnitude of the power in the strongest one of the positive and negative frequency components in each spectrum in said sequence;

determining the average value of said power;

setting a threshold level at a first predetermined magnitude above said average value of said power;

comparing the power of the strongest positive frequency component, designated the positive peak value, to the power of the strongest negative frequency component, designated the negative peak value in each spectrum, so long as either the positive peak value or the negative peak value or both in each spectrum exceeds said threshold level; and providing an audible or visual indication whenever the larger of said positive and negative peak values in a spectrum exceeds said first predetermined magnitude and the larger of said positive and negative peak values in the spectrum is more than a second predetermined magnitude above the other peak value, said audible or visual indication corresponding to the detection of a bubble or particle moving in said fluid as distinguished from probe motion.

6. A method according to claim 5 wherein said step of generating a sequence of discrete Fourier spectra of said signals returned from bubbles and particles moving in the fluid and said signals due to probe motion comprises the step of providing a predetermined number of samples of said signals returned from bubbles and particles moving in the fluid and said signals due to probe motion for each spectrum in said sequence.

7. A method according to claim 6 wherein said predetermined number of samples comprises approximately 128 samples.

8. A method according to claim 5 wherein said first predetermined magnitude is approximately 15 dB and said second predetermined magnitude is approximately 10 dB.

* * * * *